United States Patent [19]

Walters

[11] Patent Number: 4,928,546

[45] Date of Patent: May 29, 1990

[54] ROBOTIC DEVICES

[76] Inventor: David A. Walters, P.O. Box 26776, Kansas City, Mo. 64196

[21] Appl. No.: 233,333

[22] Filed: Aug. 17, 1988

[51] Int. Cl.⁵ ............................ A61F 2/58; B25J 17/02
[52] U.S. Cl. ......................................... 74/479; 74/500.5; 403/122; 403/128; 623/57; 623/62; 901/21; 901/29
[58] Field of Search ............. 74/469, 479, 500.5; 403/122, 127, 128; 623/61, 57, 62; 901/21, 29

[56] References Cited

U.S. PATENT DOCUMENTS

| | | | |
|---|---|---|---|
| 921,833 | 5/1909 | Hespe et al. | 403/128 X |
| 3,693,288 | 9/1972 | Lewis et al. | 623/62 X |
| 4,068,763 | 1/1978 | Fletcher et al. | 623/62 X |
| 4,613,331 | 9/1986 | Jacobsen et al. | 623/62 X |
| 4,804,220 | 2/1989 | Rosheim | 901/29 X |

Primary Examiner—Allan D. Herrmann

[57] ABSTRACT

This disclosure describes a wrist capable of the range of motion and function of a human wrist, composed of a basic ball and socket joint, with the ball portion segmented vertically into as many flat portions as there are fingers to allow the first segment of each finger to attach to each ball segment, allowing independant up-down motion of the fingers, while retaining dependant motion of the fingers in the back-and-forth direction.

1 Claim, 1 Drawing Sheet

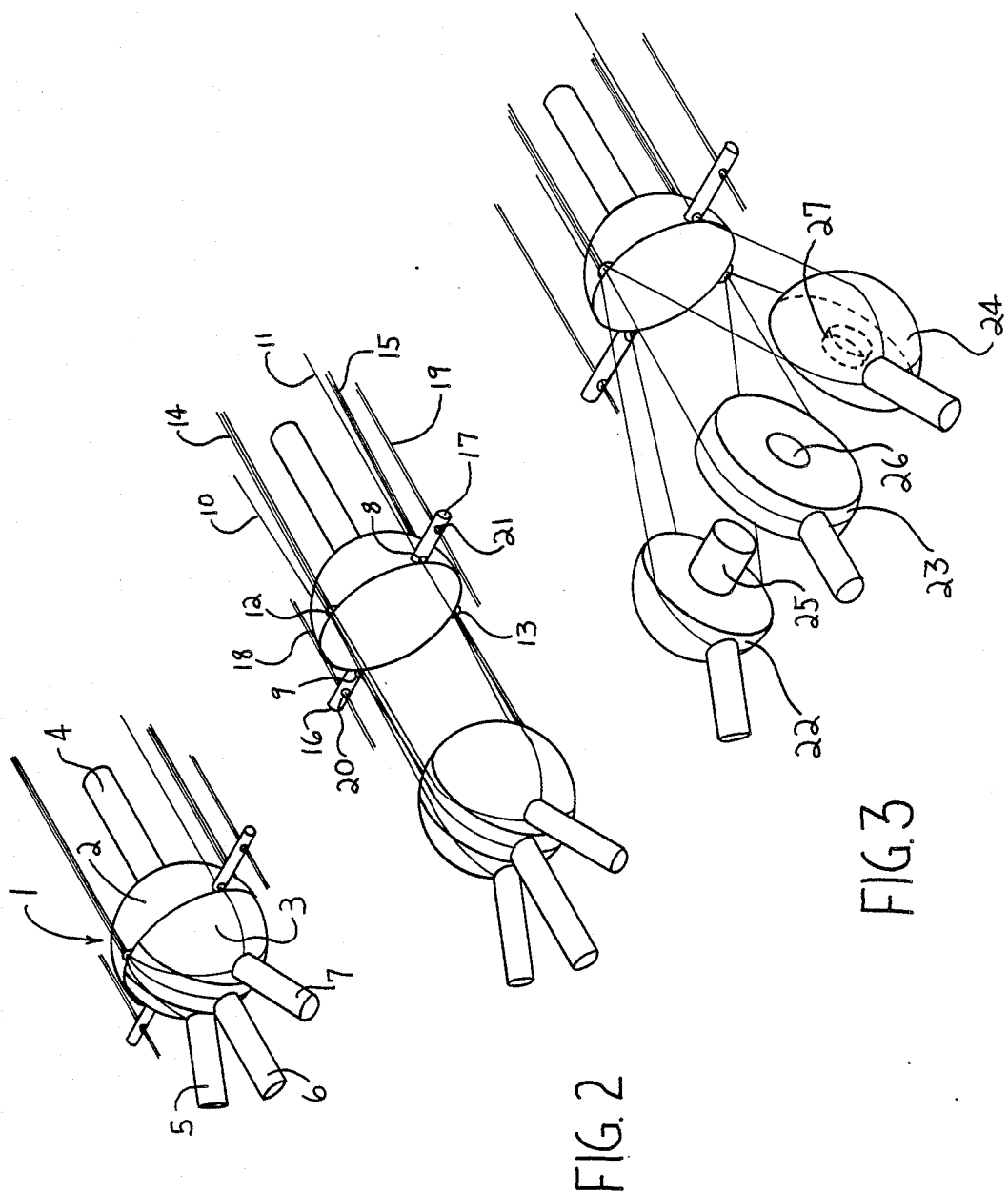

ROBOTIC DEVICES

BRIEF DESCRIPTION OF INVENTION

This disclosure describes a robotic device helpfull in the construction of prosthetic or artificial body parts.

A wrist is described that will allow full motion of a human-like wrist with various numbers of fingers. It is comprised of a ball and socket joint where the ball is cut into parallel segments, each segment being attached to one finger. Attached to each segment are two cables to control up-down motion and attached to the entire ball are two cables to control back-forth motion. The socket portion, attached to the arm, contains guides for the tendons at four equally spaced points; top, bottom, right side, and left side. When tendons pull the ball right or left, all segments of the ball move together, but when the tendons pull the ball up or down, only the segment of the ball attached to the tendon that is pulled move, and each finger is attached to one segment of the wrist, allowing independent movement of the fingers up and down, but non-independent movement of the fingers right and left.

BRIEF DESCRIPTION OF DRAWINGS

FIG. 1 shows a wrist.

FIG. 2 shows an exploded view of the wrist.

FIG. 3 shows an exploded view of the ball-portion of the wrist.

DETAILED DESCRIPTION OF THE DRAWINGS

FIG. 1 shows the wrist 1. It is made up of the socket 2, and ball 3 the two main parts of the wrist. The shaft 4 attaches to the socket on the arm side of the wrist and shafts 5, 6, 7, attached to ball on the finger side of the wrist.

FIG. 2 shows guides 8, 9, that holds tendons 10, 11 in place and guides 12, 13, that hold tendon-bundles 14, 15, in place. Rods 16, 17, attached at the sides of the socket 2 allow for other cable-bundles 18, 19, to pass through guides 20, 21.

FIG. 3 shows ball segments 22, 23, 24, that can rotate up-and-down independent of one another but cannot rotate back-and-forth independent of one another. Attached to segment 22 is a cylindrical shaped pin 25, that passed through the hole 26 in segment 23 and into a hole 27 in segment 24. This pin 25 holds the segments in position when rotating.

What is claimed is:

1. An artificial wrist apparatus comprising a ball divided into n segments along n-1 parallel planes intersecting said ball, n first rods, each of said n first rods attached to each of said n segments, a half-sherical hollow lubricated socket into which said ball fits, a second rod attached to the back outer side of said socket, a lubricated cylindrical third rod attached at the circular center of the first of said n segments, a cylindrical hole through the center of each of said next n segments except the said nth segment, said nth segment with a cylindrical hole into but not through, said holes allowing said cylindrical third rod attached to said 1st segment to pass throught said n−2 segments and into said nth segment, four equally spaced guides attached equally spaced around the edge of said socket, allowing 2n+2 tendons or cables to pass through said four guides and be free to slide and be held in position by said four guides, two fourth rods attached at opposite sides of said socket, said fourth rods attached over the locations of two of said four guides attached to said socket, said two fourth rods holding additional guides for additional tendons other than the said 2n+2 tendons and said four guides, one of said 2n+2 tendons connecting to the said n=1 first rod attached to the said n=1 segment and one of said 2n+2 tendons being connected to the said n=nth first rod attached to the said n=nth segment, arranged so that said two tendons of the said 2n+2 tendons pull said ball back and forth in said socket when said two tendons are alternatly pulled, and two said 2n+2 tendons being connected to each of said first n rods connected to n segments, one of said 2n+2 tendons connected to the bottom of said first n rods and one of said 2n+2 tendons connected to the top of said n first rods, arranged so that when the said tendons are pulled, the said segment to which each said tendon is attached moves either upward or downward.

* * * * *